United States Patent
Brown et al.

(10) Patent No.: US 12,350,251 B2
(45) Date of Patent: *Jul. 8, 2025

(54) SEXUAL HEALTH ENHANCEMENT COMPOSITION

(71) Applicant: Rev Pharmaceuticals, Inc., Jackson, WY (US)

(72) Inventors: Beth Anne-Szkudlarek Brown, Plymouth, MN (US); Anthony Lemus, Villa Park, CA (US); Marnie L. Peterson, Jackson, WY (US)

(73) Assignee: REV Pharmaceuticals, Inc., Jackson, WY (US)

( * ) Notice: Subject to any disclaimer, the term of this patent is extended or adjusted under 35 U.S.C. 154(b) by 1000 days.

This patent is subject to a terminal disclaimer.

(21) Appl. No.: 16/461,477

(22) PCT Filed: Nov. 21, 2017

(86) PCT No.: PCT/US2017/062723
§ 371 (c)(1),
(2) Date: May 16, 2019

(87) PCT Pub. No.: WO2018/094377
PCT Pub. Date: May 24, 2018

(65) Prior Publication Data
US 2019/0343791 A1    Nov. 14, 2019

Related U.S. Application Data

(60) Provisional application No. 62/424,654, filed on Nov. 21, 2016.

(51) Int. Cl.
| | | |
|---|---|---|
| *A61K 31/352* | (2006.01) | |
| *A61K 9/00* | (2006.01) | |
| *A61K 31/198* | (2006.01) | |
| *A61K 31/223* | (2006.01) | |
| *A61K 47/10* | (2017.01) | |
| *A61K 47/32* | (2006.01) | |
| *A61N 1/04* | (2006.01) | |
| *A61N 1/32* | (2006.01) | |

(52) U.S. Cl.
CPC .......... *A61K 31/352* (2013.01); *A61K 9/0014* (2013.01); *A61K 31/198* (2013.01); *A61K 31/223* (2013.01); *A61K 47/10* (2013.01); *A61K 47/32* (2013.01); *A61N 1/327* (2013.01); *A61N 1/0412* (2013.01); *A61N 1/0492* (2013.01)

(58) Field of Classification Search
CPC .. A61K 31/352; A61K 9/0014; A61K 31/198; A61K 47/10; A61K 47/32; A61K 31/223; A61K 47/14; A61N 1/327; A61N 1/0412; A61N 1/0492
See application file for complete search history.

(56) References Cited

U.S. PATENT DOCUMENTS

| | | | |
|---|---|---|---|
| 5,208,031 A | 5/1993 | Kelly | |
| 5,595,753 A | 1/1997 | Hechtman | |
| 5,804,596 A * | 9/1998 | Majeed | A61P 3/04 514/455 |
| 7,128,930 B1 * | 10/2006 | Sacks | A61P 15/00 514/474 |
| 2003/0028169 A1 * | 2/2003 | Fossel | A61K 8/44 514/880 |
| 2007/0059266 A1 | 3/2007 | Ahmad et al. | |
| 2012/0009283 A1 * | 1/2012 | Bombardelli | A61P 15/10 424/745 |
| 2014/0303681 A1 | 10/2014 | Khan et al. | |
| 2017/0281581 A1 | 10/2017 | Brown et al. | |

OTHER PUBLICATIONS

Mulhall et al. J. of Urology, 1997, vol. 158, pp. 1752-1759.*
Mulhall et al. ((1997), Intracavernosal Forskolin: Role in Management of Vasculogenic impotence resistant to standard 3-agent pharmacotherapy, J. of Urology, 158, 1752-1759, (Year: 1997).*

* cited by examiner

*Primary Examiner* — Kortney L. Klinkel
*Assistant Examiner* — Dawanna Shar-Day White
(74) *Attorney, Agent, or Firm* — Kagan Binder, PLLC

(57) ABSTRACT

A topical composition and method comprising administering physiological effective amounts of at least two active components forskolin combined with one or more lubricating base components. Active components may include one or more of L-arginine free base, hydrochloride salt, ethyl ester or combinations thereof.

12 Claims, 1 Drawing Sheet

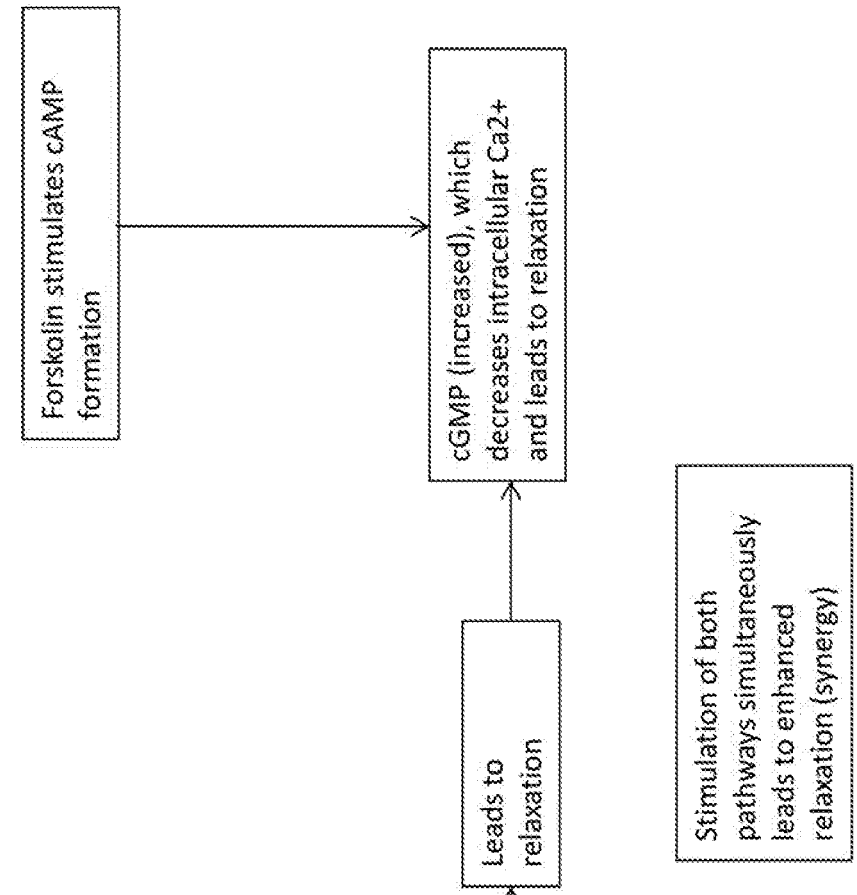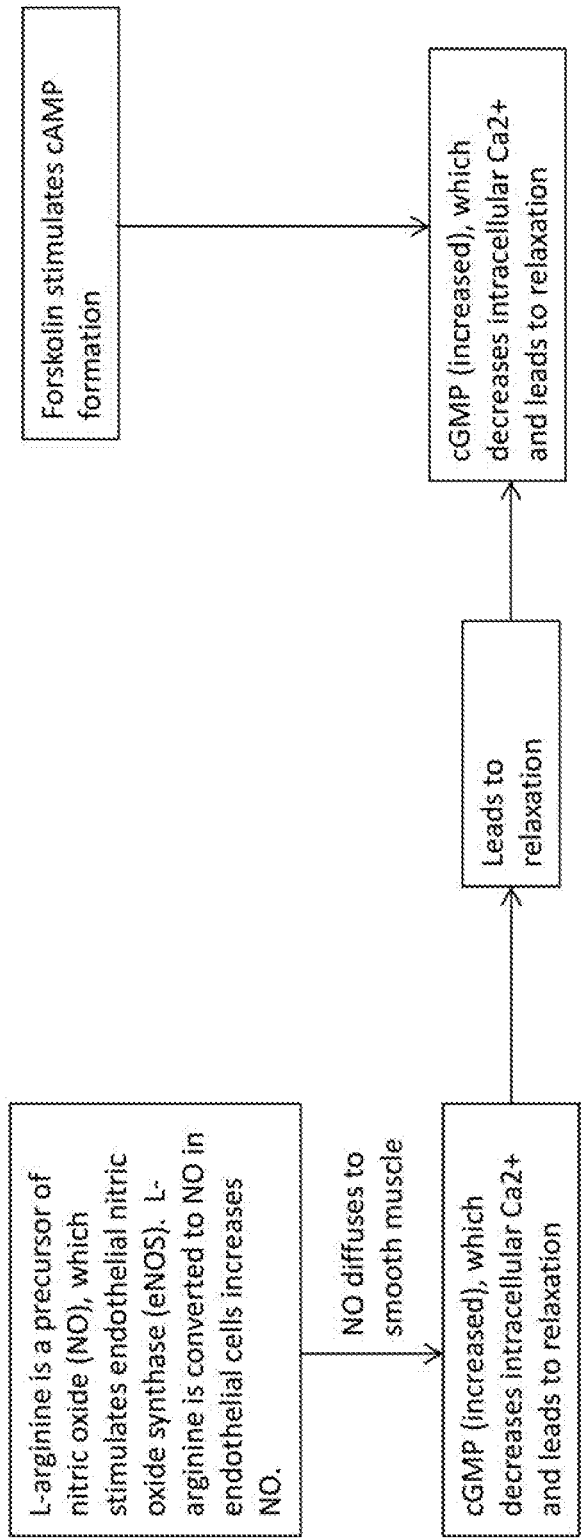

SEXUAL HEALTH ENHANCEMENT COMPOSITION

PRIORITY

This application claims priority to International Application No. PCT/US2017/062723, filed on Nov. 21, 2017, which claims the benefit of U.S. Provisional Patent Application Ser. No. 62/372,504, filed Aug. 9, 2016, the entire disclosures of which are incorporated by reference for all purposes.

BACKGROUND

Sexual dysfunction is a common malady for both women and men. Reports indicate that as many as 43% of women and 31% of men report some degree of sexual dysfunction or dissatisfaction with their sexual experiences. To date, there is a variety of prescribed drugs and over the counter nutraceutical-based products to deal with complex and multifactorial sexual dysfunction problems. Due to the often unpleasant side effects related to current drugs and nutraceutical products, there continues to be an unmet need for a nutraceutical-based product that may satisfactorily affect multiple, parallel pathways leading to erection and/or vulvovaginal stimulation and desirably impact the complex and multifactorial pathophysiology of sexual dysfunction.

Several naturally-derived compounds including, for example, yohimbine, citrulline, L-arginine, adenosine monophosphate (AMP), and forskolin have been reported to treat sexual dysfunction such as, for example, erectile dysfunction (ED). In particular, yohimbine, isolated from the bark of the West African tree, Coryanthe yohimbe, was used for the treatment of ED in a double-blind, placebo-controlled, three way crossover, randomized clinical trial to compare the efficacy and safety of the combination of L-arginine glutamate and of yohimbine hydrochloride. In these studies, the combination of oral L-arginine glutamate and yohimbine was statistically better than placebo to treat ED, especially in men with mild to moderate ED. However, due to undesirable side effects of yohimbine such as hypertension, anxiety, maniac symptoms and interactions with commonly used medications, the use of yohimbine in ED is limited.

L-citrulline, isolated from watermelons and marketed under tradename STIMULIN, has been reported to treat ED; however, this compound's mode of action has not been carefully studied.

L-arginine has been studied for treatment of ED. L-arginine is available in numerous commercially available products both oral and topical. However, the effectiveness of these products has not been carefully studied with appropriate pharmacokinetic and pharmacodynamic considerations.

Adenosine monophosphate (AMP) has important functions in penile erection and can directly reduce intracellular calcium concentrations in smooth muscle causing relaxation in a nitric oxide (NO) independent pathway. AMP can also mediate erectile initiation and maintenance through the generation of NO.

SUMMARY

The present disclosure is generally directed to an on demand combination product of a nitrous oxide (NO) donor and an adenosine donor that may be used to enhance both women's and/or men's sexual health.

One embodiment of this disclosure is a topical composition comprising physiological effective amounts of at least two active components, L-arginine or a derivative (preferably as the free base, hydrochloride salt or ethyl ester) and forskolin, combined with lubricating base components comprising, for example, lubricating pharmaceutically acceptable glycols.

Another embodiment of this disclosure is a topical compositional consisting essential of physiological effective amounts of at least two active components, L-arginine or a derivative (preferably as the free base, hydrochloride salt or ethyl ester) and forskolin, combined with lubricating base components comprising, for example, lubricating pharmaceutically acceptable glycols.

Still another embodiment of this disclosure is a topical composition consisting of effective amounts of L-arginine or a derivative (preferably as the free base, hydrochloride salt, ethyl ester, or a combination thereof) and forskolin in a gel, combined with lubricating base component comprising, for example, lubricating pharmaceutically acceptable glycols.

In each of these embodiments, the effective amount of L-arginine or a derivative (preferably as the free base, hydrochloride salt or ethyl ester) may be about 15-80 wt %, preferably about 20-40 wt %, or more preferably about 30 wt %, based on the weight of the topical composition. An effective amount of forskolin may be about 0.01-1 wt %, preferably about 0.1-0.5 wt %, or more preferably about 0.1 wt %, based on the weight of the topical composition.

In some embodiments, an amount of base components, such as, for example, glycols, in the composition may be about 19-85 wt %, preferably about 60-80 wt %, or more preferably about 60-70 wt %, based on the total weight of the topical composition.

Suitable base components include, for example, glycols (e.g. propylene glycol USP and/or polyethylene glycol), oil-in-water emulsions, water-in-oil emulsions, lipophilic foams, water, anhydrous silicone base, lipophilic foam base, transdermal cream base and mineral oils. In some embodiments, the base components include a base selected from oil-in-water emulsion or water-in oil-emulsion, anhydrous silicone base, lipophilic foam base, or transdermal cream base.

When the base components are glycols, the glycols may be selected from, for example, propylene glycol, polyethylene glycol 400 NF, butylene glycol, ethylene glycol, diethylene glycol, or pentylene glycol. In some embodiments, the lubricating base composition comprises about 75 wt % propylene glycol and about 25 wt % polyethylene glycol 400 NF based on the weight of the lubricating base components. In yet another embodiment the lubricating base composition comprises greater than 75 wt % propylene glycol and less than about 25 wt % polyethylene glycol. In a further embodiment, the lubricating base composition comprises less than 75 wt % propylene glycol and greater than about 25 wt % polyethylene glycol. In still other embodiments, butylene glycol, ethylene glycol, diethylene glycol, or pentylene glycol may be present in amounts of from about 25 wt % to about 75 wt %.

In other embodiments, the topical composition may include one or more dermal penetration enhancers. Suitable dermal penetration enhancers include, for example, volatile oils (e.g. essential oils), fixed oils (e.g. fatty acids) and polysaccharides.

In still other embodiments, acceptable topical formulations may be in the form of gels, creams, foams, lotions, ointments, or solutions having components that may include, for example, mineral oils, benzoyl peroxide, diethanolamine, monoethanolamine, triethanolamine, dioxin, parabens, phthalates, sodium lauryl sulfate, sodium laureth sulfate, tridosan, avobenzone, benzphenone, ethoxycinnamate, or PABA.

In an example embodiment, a topical composition comprises an effective amount of L-arginine and forskolin to drive Pathway 1 (described below), to increase nitric oxide (NO) production, increased blood flow by creating nitric oxide, or to drive Pathway 2 (described below), to increase cAMP induced relaxation, relaxation state for stimulation (enhanced relaxation), or both Pathway 1 and Pathway 2 and provide sexual health enhancement in both men and women.

Pathway 1:

Relaxation of the smooth muscle cells is followed by engorgement of the cavernous sinusoids, which occurs by several molecular mechanisms. The activation of the parasympathetic nervous system and cholinergic output causes a stimulation of endothelial nitric oxide synthase (eNOS), which increases the production of NO in the endothelial cells that diffuses to smooth muscle tissues. L-arginine is a physiological precursor of nitric oxide (NO), which stimulates eNOS. Increased NO in smooth muscle cells decreases intracellular calcium concentrations via cyclic guanosine monophosphate (cGMP), which leads to relaxation.

Similarly, in women (following sexual stimulation), neurotransmitters including NO are released modulating smooth muscle relaxation of the clitoral cavernosal artery and vaginal vascular and non-vascular smooth muscle. The effects of NO and cGMP on smooth muscle relaxation lead to clitoral engorgement, vaginal transudate, vaginal length and luminal diameter. L-arginine is a physiological precursor of nitric oxide (NO), which stimulates eNOS. Increased NO in smooth muscle cells decreases intracellular calcium concentrations via cGMP, which leads to relaxation.

Pathway 2:

In addition to NO, cyclic adenosine monophosphate (cAMP) also has important functions in penile erection. cAMP can directly reduce intracellular calcium concentrations in smooth muscle causing relaxation in a NO-independent pathway. Naturally occurring prostaglandin E1 (PGE1) binds to smooth muscle cell surface prostaglandin receptors and activate adenylate cyclase to convert ATP to cAMP resulting in these effects. cAMP can also induce the phosphorylation of neuronal NO synthase (nNOS) via cAMP-dependent protein kinase (PKA), which mediates erectile initiation and maintenance through the generation of NO. Based on these important biological processes, natural products such as adenosine donors (purines) and/or forskolin (adenylate cyclase inducers) have important "synergistic" effects with L-arginine (precursor of NO) on penile tissues causing an erection In addition to NO, cAMP has also been determined to relax female genital tissues via activation by a vasoactive intestinal polypeptide (VIP). In addition, inhibition of the degradation of cAMP by phosphodiesterase 4 (PDE4) a cAMP-specific degrading enzyme expressed in the vagina and clitoris was shown to increase clitoral blood flow in rat studies. As in men, natural products such as adenosine donors (purines, cAMP) and/or forskolin (adenylate cyclase inducers) have important "synergistic" effects with L-arginine (precursor of NO) on clitoral and vaginal tissues causing increased blood flow, engorgement of clitoral and vaginal tissue and arousal (vaginal lubrication and elongation).

An example of a sexual health composition includes a packaged composition comprising a single use sachet containing a topical gel composition having physiological effective amounts of L-arginine and forskolin, wherein the gel comprises pharmaceutically acceptable additives mineral oils, benzoyl peroxide, diethanolamine, monoethanolamine, triethanolamine, dioxin, parabens, phthalates, sodium lauryl sulfate, sodium laureth sulfate, tridosan, avobenzone, benzphenone, ethoxycinnamate, or PABA.

An example method of enhancing sexual health comprises topically administering an effective amount of a topical composition consisting essentially of L-arginine ethyl ester and forskolin to a subject, wherein the effective amount of L-arginine ethyl ester and forskolin generates nitric oxide for increased blood flow in the subject, or provides a relaxation state for stimulation of the subject, or both increased blood flow and relaxation state of the subject.

A method of enhancing sexual health comprises topically administering an effective amount of a topical composition consisting essentially of L-arginine ethyl ester and forskolin to a subject in combination with use of a transdermal electrically polarized conductive pad attached to an electro-stimulation power controlled device, wherein the effective amount of L-arginine ethyl ester and forskolin in combination with an electric field (or current) enhances skin penetration that generates nitric oxide for increased blood flow in the subject, or provides a relaxation state for stimulation of the subject, or provides both increased blood flow and relaxation state of the subject.

DESCRIPTION OF THE DRAWINGS

FIG. 1 is a diagram that illustrates biological processes that have synergistic effects with L-arginine and forskolin.

DETAILED DESCRIPTION

Forskolin, a diterpene natural product that is produced by the Indian Coleus plant, *Coleus forskohlii*, has been used to raise levels of cyclic adenosine monophosphate (cAMP) in the study and research of cell physiology. Forskolin activates the enzyme, adenylyl cyclase, and increases intracellular levels of cAMP.

Important molecular mechanisms of sexual stimulation may include activation of the parasympathetic nervous system, which causes stimulation of endothelial nitric oxide synthase (eNOS), which increases the production of NO in the endothelial cells. NO diffuses to smooth muscle tissues causing relaxation and erection.

L-arginine is a physiological precursor of nitric oxide (NO), which stimulates eNOS. High doses can restore NOS activity in conditions with endothelial cell dysfunction such as aging, atherosclerosis and diabetes mellitus. Forskolin stimulates cAMP formation and activates nNOS phosphorylation. Based on these important biological processes, natural products such as adenosine donors (purines) and/or forskolin (adenylate cyclase inducers), may have important "synergistic" effects with L-arginine (precursor of NO) on, for example, penile tissues causing an erection. The diagram in FIG. 1 highlights these pathways.

L-arginine free base has been studied for treatment of ED. L-arginine is a physiological precursor of nitric oxide (NO) and stimulates eNOS. L-arginine is available in numerous commercially available products in both oral and topical formulations. However, the effectiveness of these products has not been carefully studied with appropriate pharmacokinetic and pharmacodynamic considerations. High oral doses (>6 gm) are required to restore eNOS activity in conditions with endothelial dysfunction such as aging, atherosclerosis and diabetes mellitus. L-Arginine is a zwitter ion and having the properties of a zwitter ion it cannot cross human squamous epithelium to any significant degree. Some reported L-arginine preparations may contain menthol which is an irritant to human skin. By irritating the skin these products will allow some of the L-arginine to cross the skin barrier but again not to any significant degree. In some embodiments, L arginine hydrochloride salt may be substituted for the L-arginine free base. In other embodiments, in order to nullify the charge effect for example, L-arginine ethyl ester may be substituted for the L-arginine free base because the ethyl ester compound crosses squamous epithelium to a significant degree. For example, US Patent Application Pub. No. 2013/0184233 to Carter et al., "Personal Lubricant Compositions" reports a skin lubricant containing L-arginine ethyl ester. In another example, U.S. Pat. No. 7,629,384 to Fossel et. al., "Topical Delivery of L-arginine to Cause Beneficial Effects" reports a penetrating cream containing L-arginine along with sodium chloride or other salts at concentrations sufficient to produce a hostile biophysical environment and when applied to the penis induced a firm and natural erection. Intrigue Laboratories have developed a proprietary L-arginine ethyl ester based cream (40% Aquaphor) to enhance penetration of L-arginine for the treatment of sexual dysfunction in women.

Administration of L-arginine by intravenous infusion (IV) or orally at doses of from about 6 to about 30 gm induced peripheral vasodilation in humans and improved endothelium-dependent vasodilation, resulting in improved muscle blood flow.

L-arginine hydrochloride (HCl) has known physiological properties including:

L-arginine HCl was administered orally (12 capsules of 0.5 gm of L-arginine HCL) Bioavailability was 50 to 87% with a time to Cmax of 40 to 60 minutes Mean Cmax: 623 and 822 ttmol/L for 30 gm and 6 gm IV, and 310+/−152 μmol/L for 6 gm oral Half-life 60 (IV) to 90 (PO) minutes No significant changes in hemodynamics at 6 gm doses; blood pressure and total peripheral resistance were significantly decreased after 30 gm IV Increased urinary cGMP and nitrate excretion (correlate with plasma concentrations) with about from 6 gm to about 30 gm IV, causing significant increases Numerous over the counter products (gels and creams) are available with or without other agents such as ginseng, niacin and L-citrulline (at concentrations up to 5%).

Since an oral dose of 10 gm of L-arginine produces a peak arginine plasma concentration of 200 to 300 μM and the Km of NOS activity for endothelial cells is approximately 30 to 40 μM, a 10 gm oral dose produces plasma concentrations that are 10-fold above the Km. Therefore, topical administration of arginine needs to be delivered at concentrations greater than about 30 to 40 μM to achieve the desired physiological effects. Suitable topical formulations should deliver at least about 50 to 70 mg/L (50 to 70 μg/ml) to the endothelial cell membrane to achieve desired effective amounts of arginine. In some embodiments, the L-arginine includes about 20 wt % to 40 wt % of the total weigh of the topical composition.

Forskolin is a naturally occurring alkaloid derived from the Indian herb *Coleus forskohlii* that has been shown to induce smooth muscle relaxation in in vitro studies using canine corporeal tissue and penile erection after intracavernosal administration in a canine model. Forskolin binds directly and stimulates adenylate cyclase increasing cAMP concentrations, and can directly reduce intracellular calcium concentrations in smooth muscle causing relaxation in a NO-independent pathway. cAMP formation by forskolin also activates nNOS phosphorylation which may contribute to sustained erection in concert with phosphorylated eNOS stimulation.

The activity of forskolin was studied in vitro and in vivo in humans and animals compared to PGE1, papaverine and phentolamine. In vitro forskolin and prostaglandin E1 alone caused concentration dependent relaxation of human CC with an EC50 of approximately 200 nm and 16 nm, respectively. When forskolin and prostaglandin E1 were combined, the concentration response curve for relaxation shifted to the left. cAMP production was highest in cells treated with prostaglandin E1 and forskolin and was unaffected by papaverine or phentolamine. In three animals (New Zealand White rabbits) administered intracavernosal forskolin, equilibrium intracavernosal pressure and duration of erection had a dose dependent increase.

Forskolin is water soluble and affects multiple different pathways to increase cAMP which has synergistic activity with prostaglandin E1, papaverine and phentolamine. Forskolin may also have synergistic activity with L arginine (NO donor); (and also increase the efficacy PDES inhibitors). In some embodiments, the forskolin is in a pure state and "pure", when used with respect to a material containing forskolin, means having at least a technical grade of purity or at least a reagent grade of purity. Suitable purity includes ≥70%, 75%, 80%, 85%, 90%, 95% or 99% pure forskolin. In other embodiments, the forskolin is in a crude state and "crude", when used with respect to a material containing forskolin, means forskolin that has not been fully refined and can contain components in addition to forskolin having a purity of ≥40%, 45%, 50%, 55%, 60%, or 65% pure forskolin.

Suitable dermal penetration enhancers include, for example, volatile oils (e.g. essential oils), fixed oils (e.g. fatty acids) and polysaccharides. Essential oils are volatile, odoriferous substances found in the flowers, fruit, leaves and roots of certain plants. Fatty acids, on the other hand, are composed of aliphatic hydrocarbon chains, which can be either saturated or unsaturated, and include a terminal carboxyl group.

Essential oils are a complex mixture of many diverse and unique chemical compounds. Essential oils can include compounds classified as:

nitrogen- and sulphur-containing compounds (e.g., allyl isothiocyanate found in mustard oil);

aromatic compounds, which are benzene derivatives (e.g., eugenol which is the main constituent of clove oil);

terpenes (e.g., 1,8-cineole in eucalyptus oil) and terpenoids; and miscellaneous compounds (includes long-chain unbranched substances).

Exemplary essential oils include niaouli oil, eucalyptus oil, alpinia oxyphylla oil, turpentine oil, sweet basil and tulsi oil, cardamom oil, peppermint oil, fennel oil, and black cumin oil.

Terpenes, which is a constituent of an essential oil can be isolated from essential oils and are also suitable skin penetration enhancers. Terpenes do not have aromatic character but contains carbon and hydrogen atoms with or without oxygen. Exemplary terpenes include the following classes along with specific examples in that particular class:

TABLE 1

| Class | Example(s) of terpene | Source |
|---|---|---|
| ACYCLIC MONOTERPENES (Alcohols) | Geraniol and nerol | Geraniol is an unsaturated primary alcohol found in *geranium* and other essential oils. It is found as esters and as a glucoside, but mainly occurs in the free form. Nerol is the isomeric alcohol and is found in various essential oils, primarily in neroli and bergamot oils Palmarosa oil contains more geraniol than any other oil and for nerol it is catnip and rose oil. |
| | Linalol | Linalol is found as (+) and (−) forms in the oil of Linaloe (a plant found in Central America), but can also be found free and as esters in numerous other essential oils. Rosewood oil contains more linalol than any other oil. |
| MONOCYCLIC MONOTERPENES (Hydrocarbons) | Limonene | The optically active limonene is widespread in nature and is found in its (+) and (−) forms in various essential oils such as bergamot, caraway, lemon and orange oils. The signature oils for d-limonene and l-limonene is grapefruit and fleabane, respectively. |
| MONOCYCLIC MONOTERPENES (Alcohols) Alcohols related to α-terpineol | α-Terpineol | Found in many essential oils such as camphor, neroli and petitgrain oil. The signature oil is lemon *eucalyptus*. |
| | β-Terpineol | Isomeric with α-terpineol, but is not isolated from natural sources. Found in commercial terpineol. |
| | γ-Terpineol | Second isomer of α-terpineol and is found in at least one essential oil and commercial terpineol. |
| MONOCYCLIC MONOTERPENES (Alcohols) Alcohols derived from thymol | Menthol | Menthol is a constituent of numerous peppermint oils and is found as its (−)-form. |
| MONOCYCLIC MONOTERPENES (Alcohols) Alcohols derived from carvacrol | Carveol | Carveol is found in caraway oil. |
| MONOCYCLIC MONOTERPENES (Ketones) Ketones related to menthone | Menthone | (−) form is found in numerous peppermint oils, (+) form also occurs naturally. |
| | Pulegone | Found in pennyroyal and many other essential oils as its (+) form. |
| | iso-Pulegone | Often an accompaniment of pulegone in essential oils. |
| | Piperitone | Occurs in numerous *eucalyptus* oils as (+)- and (−) forms. |
| MONOCYCLIC MONOTERPENES (Ketones) Ketones related to carvomenthone | Carvomenthone | Isomeric with menthone and is a saturated ketone. (−) form is found in numerous essential oils. |
| | Carvone Unsaturated ketone | Occurs in its (+), (−) and (±) forms and is the main constituent of caraway and dill oils. It can also be found in spearmint oil. |
| MONOCYCLIC MONOTERPENES (Oxides) | 1,8-Cineole | Widespread in essential oils, particularly in *eucalyptus* and wormseed oil. |
| BICYCLIC MONOTERPENES (Hydrocarbons) | α-Thujene | Found in numerous essential oils. |
| BICYCLIC MONOTERPENES (Hydrocarbons) | Car-3-ene | Found in several turpentine oils. |
| BICYCLIC MONOTERPENES (Hydrocarbons) | α-Pinene | Widespread in nature, found in most essential oils of Coniferae. It is the main constituent of turpentine oil. Secreted by conifers, turpentine oil consists of resinous material dissolved in turpentine oil. |
| | β-Pinene (Nopinene) | Isomeric with α-pinene. Its signature oil is galbanum. |
| BICYCLIC MONOTERPENES (Oxygenated derivatives) | Verbenol, verbenone and verbanone | Verbenol and verbenone has been found in nature, with the latter being found in *verbena* oil. The signature oil for verbenone is rosemary verbenone. |
| BICYCLIC MONOTERPENES (Ketones - camphane | Camphor | Not widely distributed in nature, is the major constituent of camphor oil, obtained from the leaves and wood of |

TABLE 1-continued

| Class | Example(s) of terpene | Source |
| --- | --- | --- |
| group) | | the camphor tree (*Cinnamomum camphora*). |
| BICYCLIC MONOTERPENES (Ketones - fenchane group | Fenchone | Occurs as the optically active forms in fennel, thuja and cedar leaf oils. |
| SESQUITERPENES (Alcohol) | Farnesol | Widely distributed in flower oils, in particular those of the *acacia, cyclamen* and the rose. |
| | Nerolidol | Isomeric with farnesol and found in neroli oil. |
| | (−) Guaiol | A crystalline alcohol found in *guaiacum* wood oil. |
| | (+) Cedrol | Cedarwood oil. |
| | (−) α-Bisabolol | Camomile oil. |
| SESQUITERPENES (Hydrocarbon) | Bisabolene | Widespread in nature, found in bergamot and myrrh oils. Also in many other essential oils. |
| | The Azulenes (Unsaturated hydrocarbons) | All hydrocarbons are derived from azulene ($C_{10}H_8$), a parent hydrocarbon. Most of those attained from natural origin have the molecular formula $C_{15}H_{18}$. Azulenes is responsible for the blue color of certain essential oils, or when essential oils become blue/violet when undergoing processes which might result in dehydrogenation |
| | (+) Longifolene | Tricyclic sesquiterpene found in the essential oil of *Pinus longifolia*. |
| | β-Caryophyllene | Main hydrocarbon constituent of clove oil. |
| | (+)- | *Eucalyptus* oil. |
| | (+) β-Cedrene | Cedarwood oil. |
| ACYCLIC DITERPENES (Alcohol) | Phytol | Found in rosemary oil. |
| ACYCLIC TRITERPENES (Hydrocarbon) | Squalene | It is found in the unsaponifiable fraction of shark liver oil and in several plant sources such as vegetable oils and several fungi. Jasmine is the signature oil. |

In some embodiments, the terpene menthol is used as a skin penetration enhancer in a composition containing L-arginine.

Exemplary fixed oils or fatty acids include fish oil, fatty acids from algae and phospholipids (e.g. phosphatidylglycerol, phosphatidylethanolamine, phosphatidylcholine, phosphatidylserine, phosphatidic acid, phosphadtylinositol).

Exemplary polysaccharides (polymer of simple sugars and their derivatives) as skin penetration enhancers include chitosan, aloe vera gel or aloe vera juice.

Other skin penetration enhancers can include methyl salicylate, capsaicin (trans-8-which is an alkaloid derived from hot chili peppers, belonging from the genus *Capsicum* of the *Solanaceae* family), vitamin E (α-tocopherol and methyl salicylate, oil of wintergreen or wintergreen oil is an organic ester naturally produced by many species of plants, particularly wintergreens).

Skin penetration enhancers such as terpenes and phospholipids can also be used to prepare vesicles (e.g. liposomes, ivansomes and ethosomes) for transdermal delivery. In other embodiments, essential oils can also be incorporated into patches for transdermal delivery. Exemplary oils can include any of the disclosed essential oils. In some embodiments, the essential oils used in patches include menthol oil, lemon grass oil, clove oil, eucalyptus oil or combinations thereof. The transdermal patches used can include matrix, microreservoir, reservoir, adhesive and membrane-matrix hybrid type patches.

In some embodiments, the disclosed composition is delivered topically to the skin. Unfortunately, dermal and transdermal delivery can be limited by the permeability of the substance or composition. To enhance or improve the absorption or delivery of L-arginine through the skin, skin penetration enhancers may be included. Both chemical and/or physical approaches can be used to enhance the penetration of substances across the skin. A skin penetration enhancer may include compounds that assist in the effective delivery of a desired ingredient (e.g. L-arginine) into the skin. Exemplary skin penetration enhances include volatile oils (e.g. essential oils), fixed oils (e.g. fatty acids) and polysaccharides. Essential oils are volatile, odoriferous substances found in the flowers, fruit, leaves and roots of certain plants. Fatty acids, on the other hand, are composed of aliphatic hydrocarbon chains, which can be either saturated or unsaturated, and include a terminal carboxyl group.

Like L-arginine, electrostimulation may also facilitate blood vessel dilation. In contrast to electrophoresis which requires actives to be in the ionized state for delivery, L-arginine and electrostimulation may allow non-ionized actives to be absorbed to a greater extent than in their absence. In some embodiments, the topical composition is applied in combination with electro stimulation. In one embodiment this provides a method of enhancing sexual health comprising of topically administering an effective amount of a topical composition consisting essentially of L-arginine ethyl ester and forskolin to a subject in combination with use of a transdermal electrically polarized conductive pad attached to an electro-stimulation power controlled device, wherein the effective amount of L-arginine ethyl ester and forskolin in combination with an electric field (or current) enhancing skin penetration generates nitric oxide for increased blood flow in the subject, or provides a relaxation state for stimulation of the subject, or both increased blood flow and relaxation state of the subject.

EXAMPLES

Formulating/Packaging Procedures and Processes

An example of a suitable protocol for formulating L-arginine ethyl ester and forskolin in gel-based lubricants for sexual health is provided below in Table 1.

TABLE 1

| Base Ingredients | Supplier | Function | % w/v |
|---|---|---|---|
| Propylene glycol USP | Fagron | Lubricant | 75% |
| Polyethylene glycol 400 NF | Gallipot or Fagron | Lubricant | 25% |
| | | Total | 100% |
| L-arginine ethyl ester | Sigma 5 g per vial | Active ingredient | 40% |
| L-arginine ethyl ester | Sigma (same as above/below) | Active ingredients | 40% |
| Forskolin | Sigma 50 mg | | 0.2% |

TABLE 2

Formulation Schemes

| Formulation | Strength | Actives |
|---|---|---|
| 1 | Maximum | LA-EE 40% |
| 2 | Maximum | LA-EE 40%; Forskolin 0.2% |

Clinical Investigations

In a clinical investigation, unit dose sachets (3 ml) containing the formulation set out above in Table 1 were distributed randomly to volunteer self-reported healthy males (n=16, ages: 25 to 75 years) to use in their normal sexual activities. A 14 question survey was then completed anonymously using Survey Monkey post-use. 31.2% of men experienced greater firmness than normal and 81.2% of mean experienced greater than or equal to normal erection firmness. The quality of sexual experience was 75% higher than normal. 81% of men were likely to use product if available.

Performance Feedback

Buy it if Available Today - 80%
Enhanced Erection Firmness - 81%
Sex Quality better than Normal - 75%

The female partner perspective was captured in four written testimonials. "There was a positive effect on the female partner (age 51 and menopausal)"; "Beyond the lubrication it provided a tingling sensation which made the vagina more sensitive. The overall experience was the best sex in a couple years and outstanding."; "From the female (premenopausal) perspective it was outstanding. It created a tingling sense of warmth and lubrication which brought on an orgasm much faster and predictable than normal;" and "Female partner had a noticeably better than average orgasm."

It will be readily apparent to one of ordinary skill in the relevant arts that other suitable modifications and adaptations to the composition, methods and applications described herein can be made without departing from the scope of any of the embodiments. The following examples are included herewith for purposes of illustration only and are not intended to be limiting.

The invention claimed is:

1. A topical composition consisting essentially of physiological effective amounts of at least two active components comprising about 25 wt % of one or more of L-arginine hydrochloride salt, L-arginine ethyl ester or combinations thereof, and about 1 wt % of forskolin based on topical composition weight; combined with one or more lubricating base components.

2. The topical composition of claim 1 consisting of the physiological effective amounts of L-arginine hydrochloride salt, L-arginine ethyl ester, or combinations thereof, and forskolin in a gel comprising one or more lubricating base components.

3. The topical composition of claim 1 where in the lubricating base components comprising at least one lubricating pharmaceutically acceptable glycol.

4. The topical composition of claim 1 wherein the base components are selected from the group consisting of propylene glycol, polyethylene glycol 400 NF, butylene glycol, ethylene glycol, diethylene glycol, pentylene glycol, and a combination thereof, and wherein the base components comprise oil-in-water emulsions, water in-oil emulsions, anhydrous silicone bases, lipophilic foam bases, or transdermal cream bases.

5. The topical composition of claim 1 comprising about 75 wt % propylene glycol and about 25 wt % polyethylene glycol 400 NF based on lubricating base components weight.

6. The topical composition of claim 1 comprising greater than 75 wt % propylene glycol and less than about 25 wt % polyethylene glycol.

7. The topical composition of claim 1 comprising less than 75 wt % propylene glycol and greater than about 25 wt % polyethylene glycol.

8. The topical composition of claim 1 wherein the one or more base components comprise dermal penetration enhancers.

9. The topical composition of claim 1 wherein the dermal penetration enhancers comprise essential oils, fatty acids, or polysaccharides.

10. The topical composition of claim 1 wherein the base components are selected from glycols, oil-in-water emulsions, water-in-oil emulsions, lipophilic foams, water, anhydrous silicone base, lipophilic foam base, transdermal cream base, and mineral oils.

11. A topical composition comprising about 25 wt % of one or more of L-arginine hydrochloride salt, L-arginine ethyl ester, or combinations thereof, and about 1 wt % of forskolin based on topical composition weight; to provide one or more of the following conditions for sexual health enhancement: increased nitric oxide (NO) production, increased blood flow by creating nitric oxide, increased cAMP induced relaxation, relaxed state for stimulation, or enhanced relaxation.

12. A packaged sexual health composition comprising a single use sachet containing a topical gel composition about 25 wt % of one or more of L-arginine free base, hydrochloride salt, ethyl ester, or combinations thereof, and about 1 wt % of forskolin based on topical composition weight; wherein the gel comprises pharmaceutically acceptable additives selected from mineral oils, benzoyl peroxide, diethanolamine, monoethanolamine, triethanolamine, dioxin, parabens, phthalates, sodium lauryl sulfate, sodium laureth sulfate, tridosan, avobenzone, benzphenone, ethoxycinnamate, and PABA.

* * * * *